United States Patent [19]
Sciver

[11] Patent Number: 6,036,708
[45] Date of Patent: Mar. 14, 2000

[54] CUTTING STENT WITH FLEXIBLE TISSUE EXTRACTOR

[75] Inventor: Jason Van Sciver, Mountain View, Calif.

[73] Assignee: Advanced Cardiovascular Systems, Inc., Santa Clara, Calif.

[21] Appl. No.: 09/134,540

[22] Filed: Aug. 13, 1998

[51] Int. Cl.⁷ ................................................. A61B 17/22
[52] U.S. Cl. ......................... 606/159; 606/170; 606/180
[58] Field of Search .................................... 606/159, 170, 606/180, 172, 192, 193, 195; 604/22, 29, 53, 96; 623/1, 2, 12

[56] References Cited

U.S. PATENT DOCUMENTS

| | | | |
|---|---|---|---|
| 4,765,332 | 8/1988 | Fischell et al. | 128/305 |
| 4,830,003 | 5/1989 | Wolff et al. | 128/343 |
| 4,966,604 | 10/1990 | Reiss | 606/159 |
| 5,030,201 | 7/1991 | Palestrant | 604/22 |
| 5,074,841 | 12/1991 | Ademovic et al. | 604/22 |
| 5,100,425 | 3/1992 | Fischell et al. | 606/159 |
| 5,176,693 | 1/1993 | Pannek, Jr. | 606/159 |
| 5,224,945 | 7/1993 | Pannek, Jr. | 606/159 |
| 5,318,576 | 6/1994 | Plassche, Jr. et al. | 606/159 |
| 5,356,418 | 10/1994 | Shturman | 606/159 |
| 5,368,566 | 11/1994 | Crocker | 604/101 |
| 5,423,846 | 6/1995 | Fischell | 606/180 |
| 5,441,515 | 8/1995 | Khosravi et al. | 606/194 |
| 5,549,662 | 8/1996 | Fordenbacher | 623/1 |
| 5,556,408 | 9/1996 | Farhat | 606/180 |
| 5,618,299 | 4/1997 | Khosravi et al. | 606/198 |
| 5,662,671 | 9/1997 | Barbut | 606/170 |
| 5,676,685 | 10/1997 | Razavi | 606/194 |
| 5,716,410 | 2/1998 | Wang et al. | 623/12 |

FOREIGN PATENT DOCUMENTS 448859  10/1991  European Pat. Off. ............... 606/159

*Primary Examiner*—Michael Buiz
*Assistant Examiner*—Lien Ngo
*Attorney, Agent, or Firm*—Skjerven, Morrill, MacPherson, Franklin & Friel, LLP

[57] ABSTRACT

A catheter in accordance with my invention comprises a temporary self-expanding cutting stent and a retractable sheath for containing the self-expanding cutting stent. The catheter is positioned such that the self-expanding cutting stent is within a stenosis or other blockage within an artery. The retractable sheath is then retracted, and the self-expanding cutting stent expands, cutting through stenotic tissue, scar tissue, or other tissue blocking the artery. A second retractable structure, such as a coil, a ring, a screw or a second self-expanding cutting stent extends through the interior of the temporary self-expanding is cutting stent, and cuts any tissue extending through the struts of the temporary self-expanding cutting stent, and pulling that tissue to a location within the sheath. The sheath is then pushed back over the self-expanding cutting stent, and the catheter is then retracted.

26 Claims, 16 Drawing Sheets

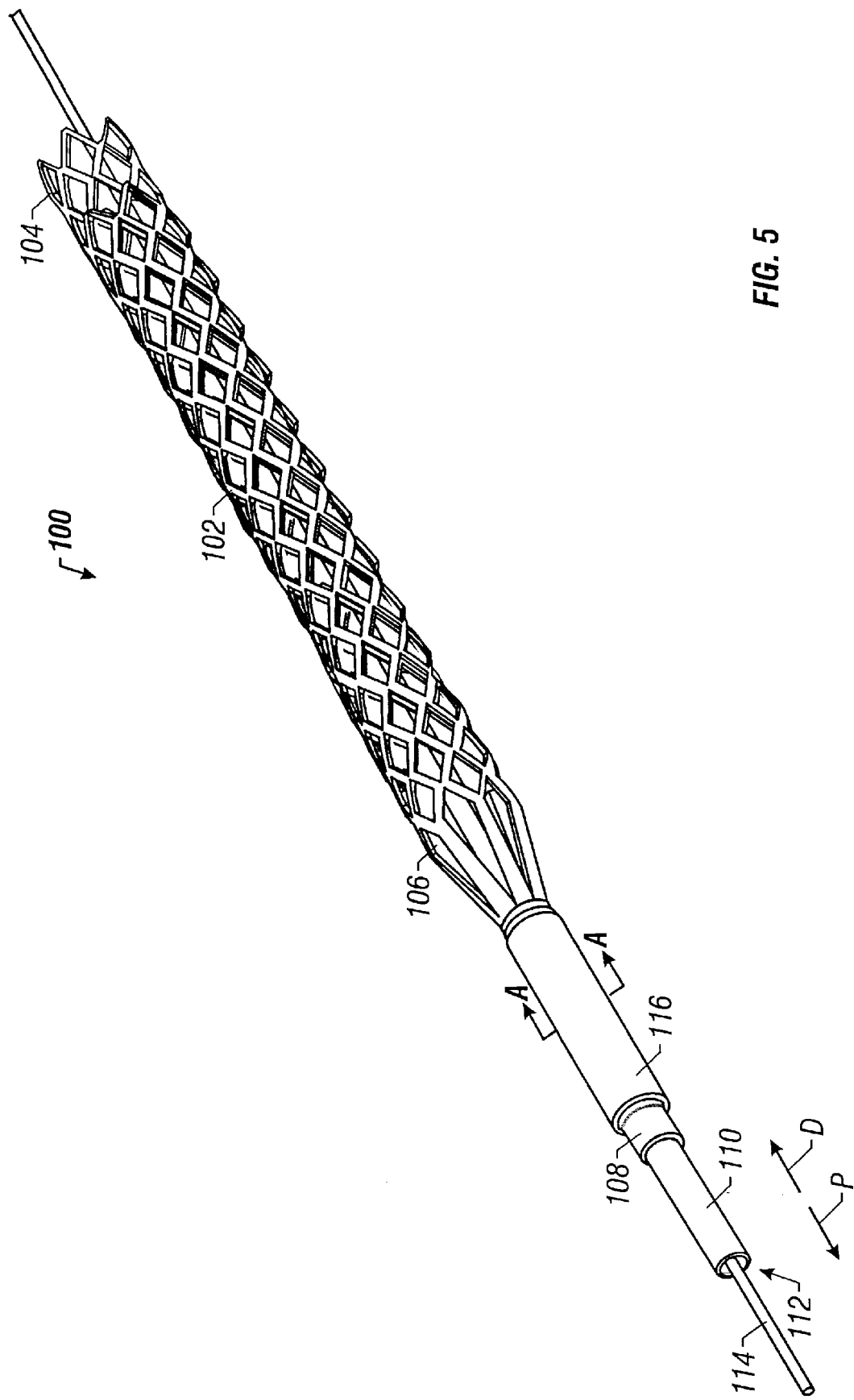

6,036,708

CUTTING STENT WITH FLEXIBLE TISSUE EXTRACTOR

BACKGROUND OF THE INVENTION

This invention pertains to apparatus for removing tissue forming blockages and constrictions in arteries, and more particularly, to apparatus for cutting and removing scar and other tissue accumulated inside stents within an artery.

Material known as plaque accumulates inside arteries, and can form a constriction, or stenosis, that blocks blood flow within the arteries. If this occurs within the coronary artery, blood flow can be obstructed in the coronary artery, thereby resulting in a heart attack, and perhaps death. Accordingly, much attention has been devoted to methods and apparatus for unblocking arteries clogged with plaque deposits.

One method for removing an obstruction in an artery is angioplasty. During angioplasty, a physician (typically a cardiologist) inserts a catheter into the patient's coronary artery. There is a balloon at the distal end of the catheter. The cardiologist inflates the balloon, thereby expanding the arterial lumen. The balloon is then deflated and the catheter is removed. Examples of angioplasty catheters are described in U.S. Pat. No. 4,323,071, issued to Simpson et al. and U.S. Pat. No. 5,769,868 issued to Yock et al.

Another method for removing an obstruction is to insert a stent in the patient's artery. A stent is a mechanical device inserted into an obstructed portion of a patient's artery which pushes the artery walls outwardly to increase the artery lumen size. Unlike a balloon catheter, a stent is typically not removed from the patient's artery after insertion. Rather, the stent remains in place to ensure that the lumen retains an appropriate caliber. FIG. 1A schematically illustrates in cross section an artery 10 with a lesion comprising atherosclerotic plaque 11, and stent 12 placed therein to maintain the desired caliber of the artery lumen. Examples of stents are discussed in U.S. Pat. No. 4,830,003, issued, to Wolff et al., U.S. Pat. No. 5,618,299 issued to Khosravi, et al., and U.S. Pat. No. 5,549,662 issued to Fordenbacher.

Unfortunately, scar tissue (e.g. tissue 14 of FIG. 1B) can accumulate within the interior of stent 12 after stent 12 is in place, thereby obstructing the artery lumen. Such tissue is typically smooth, has a consistent morphology, and deposits circumferentially at the site where stent 12 has been implanted. This tissue can block the artery and cause serious health problems, including death. Accordingly, it would be desirable to remove the tissue that accumulates within the stent.

SUMMARY

A catheter in accordance with my invention includes a self-expanding cutting stent at its distal end within a retractable sheath for containing the cutting stent. The catheter is positioned within a constriction in a patient's artery. In one embodiment, the constriction comprises scar tissue inside a permanent stent that was previously implanted in the patient. After the catheter is appropriately positioned, the retractable sheath is retracted in a proximal direction, thereby exposing the self-expanding cutting stent, and permitting the self-expanding cutting stent to expand. The self-expanding cutting stent pushes through the scar tissue within the permanent stent. A tool is then pulled through the self-expanding cutting stent to cut scar or other tissue extending through the struts of the self-expanding cutting stent and pull that tissue toward the retractable sheath. The retractable sheath is then extended back over the cutting stent to enclose the cutting stent and the cut portions of the tissue so that the cut tissue cannot flow down the patient's blood stream and cause an embolism. The catheter is then retracted.

In an alternative embodiment, the catheter is used to remove plaque or other material forming a constriction within a patient's artery that is not within a stent.

BRIEF DESCRIPTION OF THE DRAWINGS

FIG. 5 illustrates the distal end of a catheter constructed in accordance with another embodiment of my invention including inner and outer cutting stents.

DETAILED DESCRIPTION

Figure 1A:
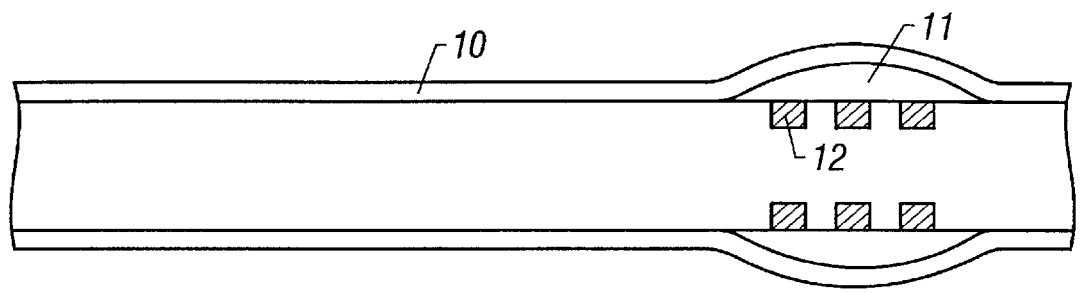
FIG. 1A illustrates an artery with a plaque deposit and a stent therein in accordance with the prior art.
Figure 1B:
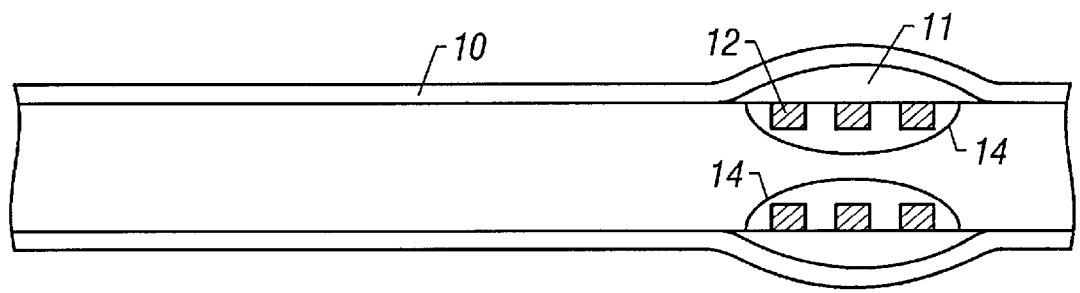
FIG. 1B illustrates an artery with a stent therein and scar tissue within the interior of the stent.

FIGS. 2 and 2A to 2C illustrate a catheter 20 in accordance with my invention having a proximal end 22 and a distal end 24. As explained below, catheter 20 is used to remove scar tissue 14 or other tissue within patient's artery 10 (see FIGS. 3A and 3B).

Catheter 20 comprises a guide wire lumen 26. A guide wire 30 is typically passed through guide wire lumen 26. Catheter 20 and guide wire 30 are then advanced into and through a patient's vascular system until a distal end 32 of guide wire 30 is at a desired location, e.g., extending through a constriction with the patient's vascular system. Catheter 20 is then advanced over guide wire 30 until distal end 24 of catheter 20 is at a desired location within the vascular system where scar tissue 14 has accumulated. (Scar tissue 14 is typically within permanent stent 12.)

Figure 2B:
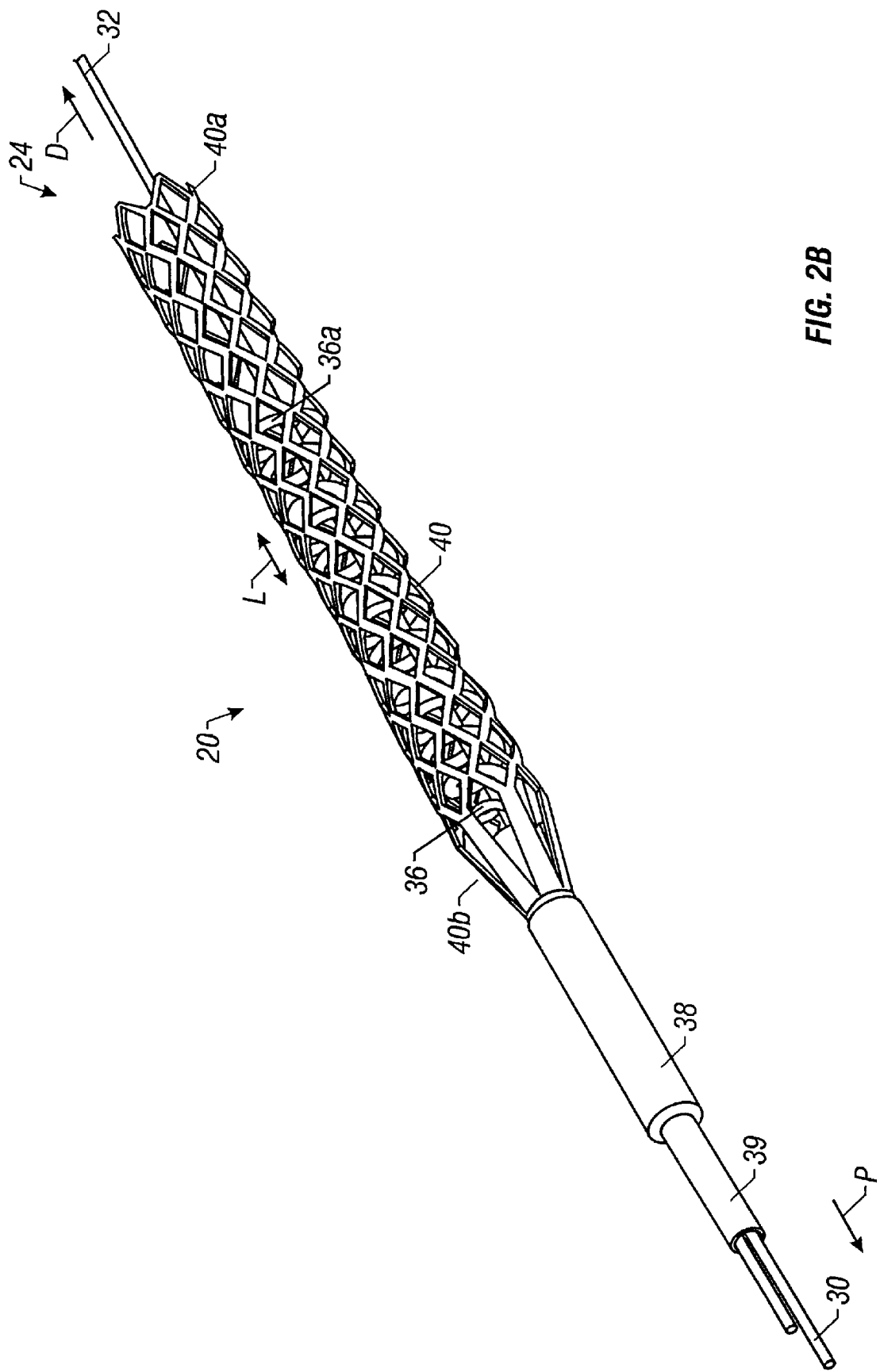
FIG. 2B illustrates the distal end of the catheter of FIG. 2.
Figure 2C:
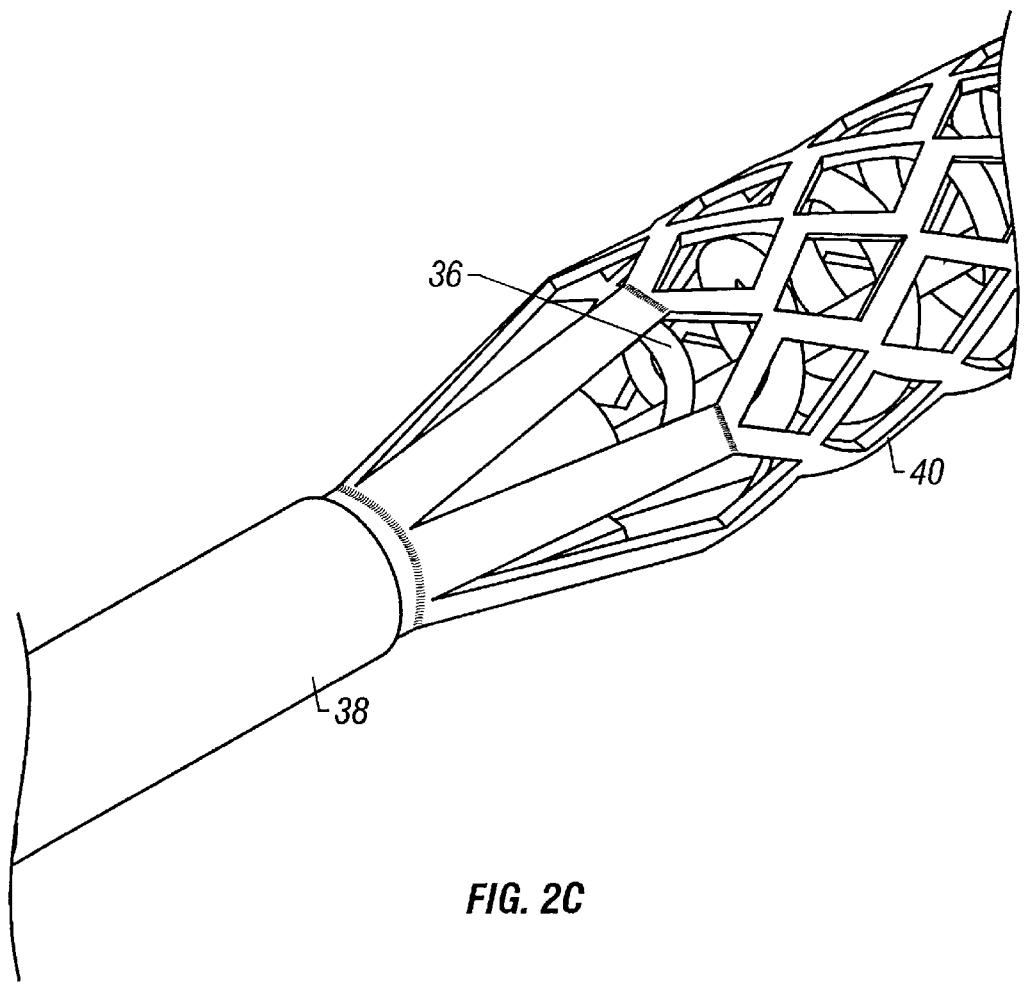
FIG. 2C is an expanded view of a portion of FIG. 2B.
Figure 3A:
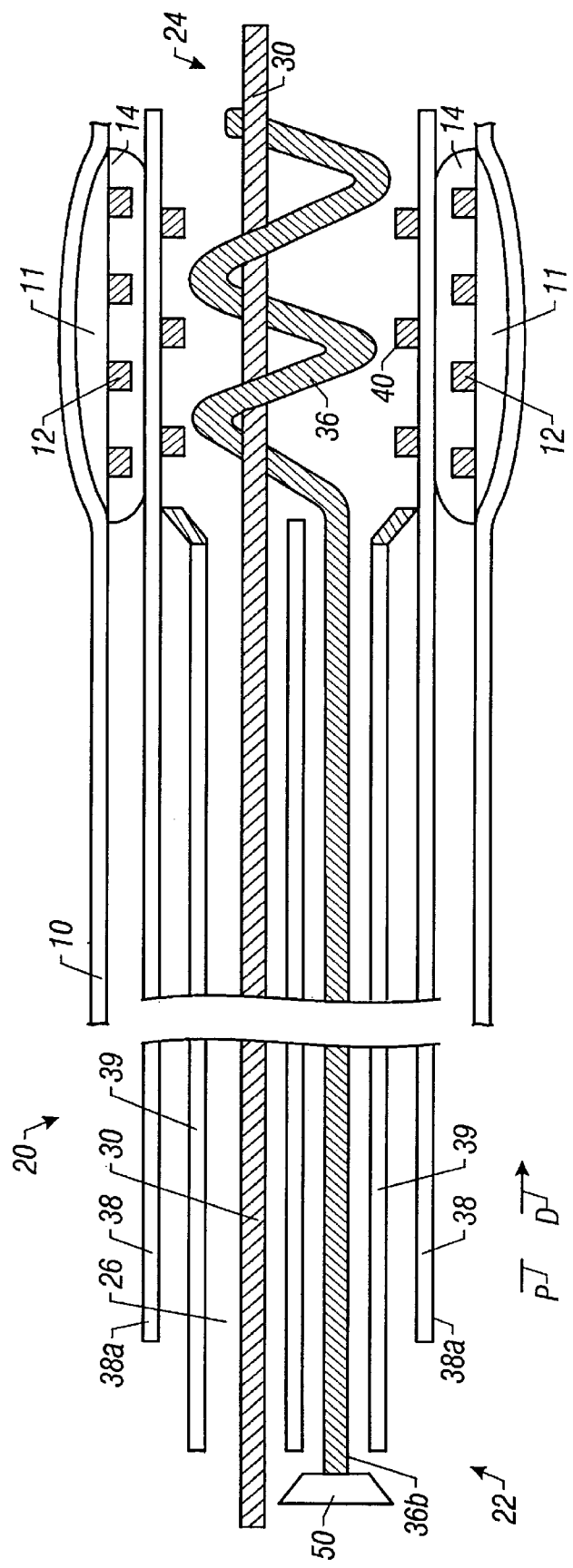
FIG. 3A illustrates the catheter of FIG. 2 after it has been inserted into a constriction within a patient.
Figure 3B:
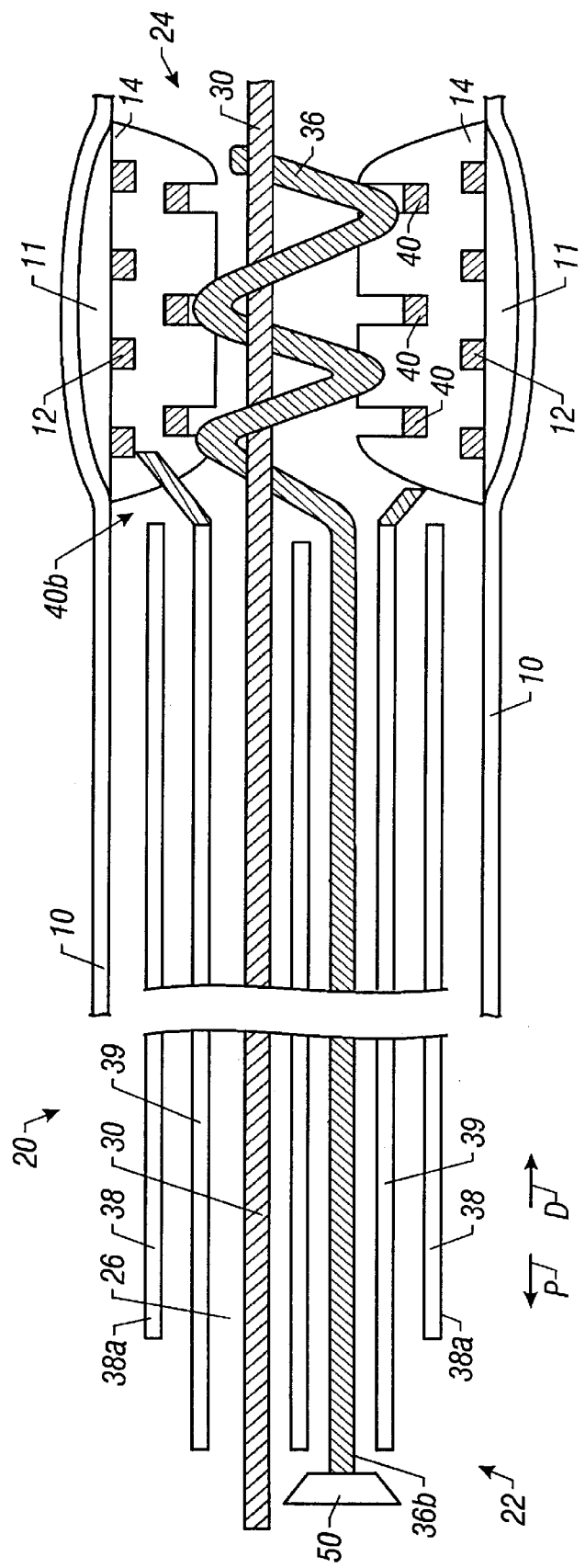
FIG. 3B illustrates the catheter of FIG. 3A after the retractable sheath of the catheter has been retracted.

Catheter 20 includes a retractable sheath 38 surrounding a shaft 39 and a self-expanding temporary cutting stent 40 extending from shaft 39. A portion 38a of sheath 38 extends proximally out of the patient. After catheter 20 is in a desired position, sheath 38 is retracted by the physician, e.g. by pulling portion 38a of sheath 38 in the proximal direction P, thereby exposing temporary cutting stent 40. Because of the spring-like nature of the struts of stent 40, after sheath 38 is retracted, self-expanding cutting stent 40 expands (FIGS. 2B and 3B). As stent 40 expands, it cuts through scar tissue 14 until stent 40 reaches the inner diameter of previously implanted permanent stent 12. Permanent stent 12 prevents cutting stent 40 from injuring the tissue of artery 10.

Thereafter, a screw 36 is advanced forward and threaded through scar tissue 42 (i.e. by rotating screw 36 and permitting screw 36 to move forward) until the distal end 36a of screw 36 reaches a distal end 40a of stent 40. Screw 36 is then rotated but held so as to prevent screw 36 from lateral motion in direction D. Screw 36 shears off any tissue protruding through the struts of cutting stent 40. This tissue is swept towards a proximal end 40b of stent 40 by the rotation of screw 36.

The material of screw 36 extends through a screw lumen 34 of catheter 20. Screw 36 is rotated by rotating the proximal end 36b of screw 36. In one embodiment, screw 36 is rotated by rotating a knob 50 affixed to proximal end 36b of screw 36.

After cutting is completed, sheath 38 is advanced over cutting stent 40 (i.e. in direction D) to collapse stent 40 and entrap the cut scar tissue. Catheter 20 is then removed from the artery with sheath 38 in place by pulling catheter 20 in proximal direction P. In this way, cut scar tissue cannot flow downstream and form another blockage in the patient's vascular system. Also, because stent 40 is collapsed within sheath 38, stent 40 will not damage patient's artery 10 as catheter 20 is withdrawn.

In one embodiment, stent 40 and screw 36 are manufactured from a shape memory alloy, e.g. a nickel-titanium alloy such as nitinol. Stent 40 is manufactured by a) providing a cylindrical Ni—Ti hypotube; b) using a laser to cut a distal portion of the Ni—Ti hypotube to form the strut pattern of stent 40; c) placing distal portion of the hypotube over an expanding mandrel; d) heating stent distal portion of the hypotube to about 550° C. for about 15 minutes; and e) quenching distal portion. The distal portion of the hypotube thus retains the shape it was in at the time it was quenched.

The Ni—Ti hypotube can be part number 809527-000 PROT-TUBE-BB-55.2×69×SAMP, available from Raychem Corporation. In one embodiment, the proximal portion of the hypotube serves as shaft 39 of catheter 20.

In an alternative embodiment, the entirety of the cylindrical hypotube is cut by a laser to form the strut pattern of stent 40 along its entire length. The hypotube is then cut into individual stent portions (e.g. on the order of about 0.5 to 1.5 cm long), the distal end of the individual stent portions are placed over an expanding mandrel, and the stent portions are heated and quenched as described above. The diameter of the proximal end of the stent portions remains substantially unchanged. The proximal end of the stent portions are then bonded onto catheter shaft 39. In this embodiment, shaft 39 can be made of an appropriate polymer such as polyethylene, and the proximal end of the stent portion is bonded onto shaft 39 with an appropriate adhesive. Alternatively, shaft 39 can be made of a combination of polyethylene surrounding a hypotube. The stent portion can be welded to the hypotube, or affixed to the shaft with an appropriate adhesive.

In one embodiment, when the hypotube is cut by a laser, the angle that the laser makes with the hypotube is sharp, so that when the hypotube is placed over a mandrel to form stent 40, the angles of the stent struts are sharp, and can easily cut into a constriction within the patient. In another embodiment, the laser simply cuts the hypotube at a right angle to the portion of the hypotube surface being cut.

Figure 8:
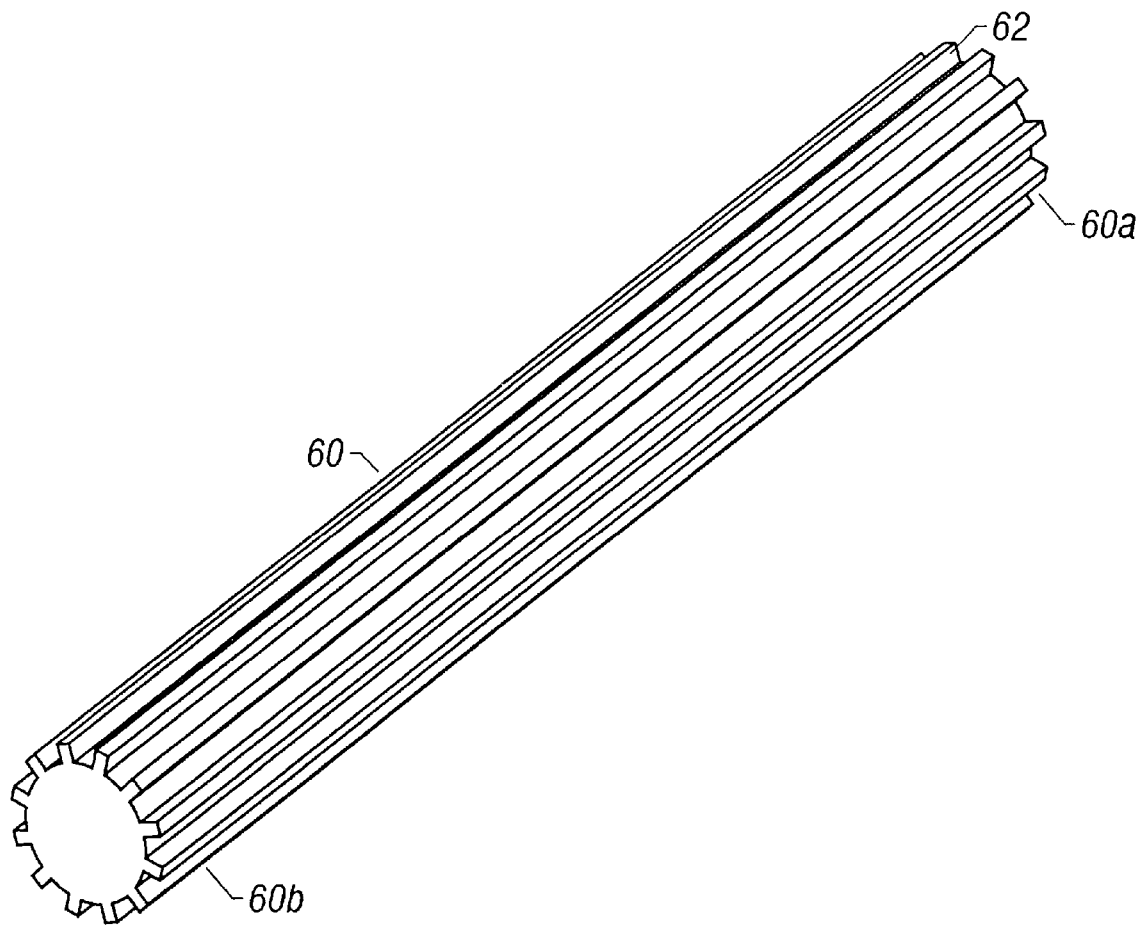
FIG. 8 illustrates tubing used to manufacture a cutting stent in accordance with my invention.
Figure 9:
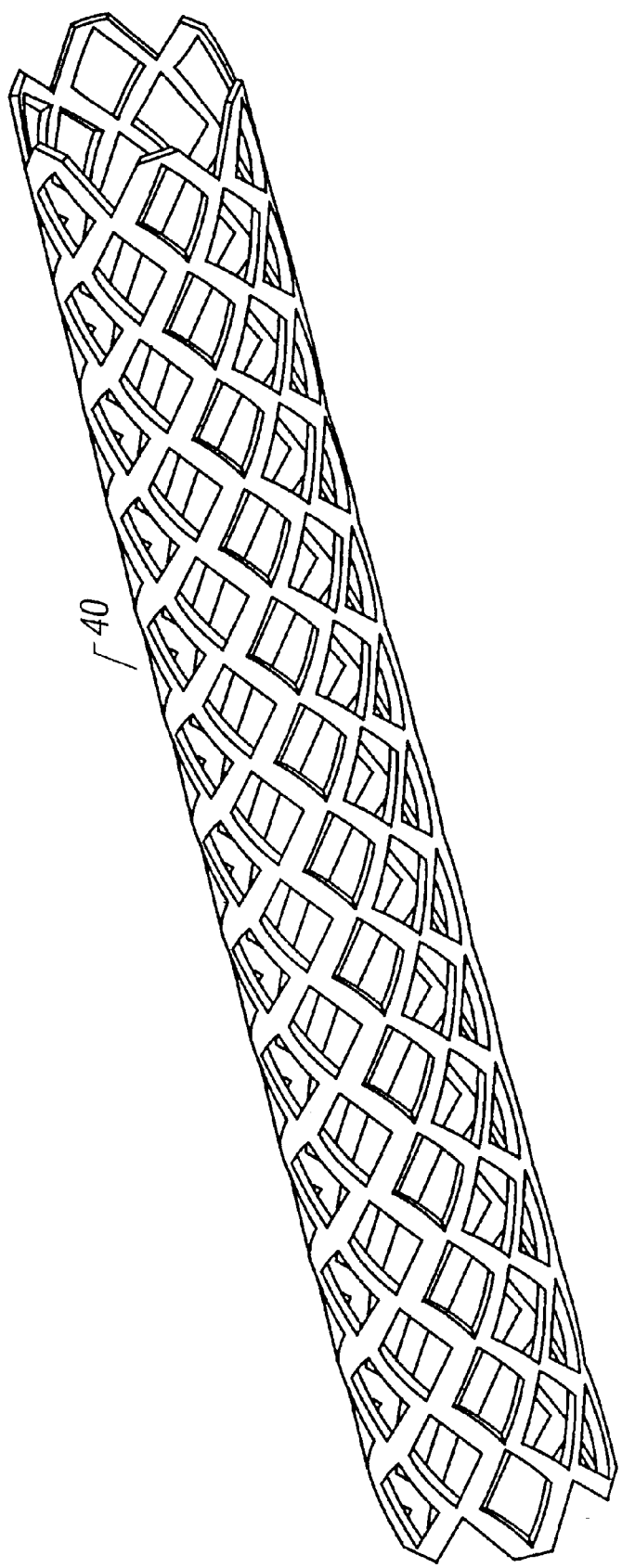
FIG. 9 illustrates the cutting stent of FIG. 2.

In yet another embodiment, prior to forming stent 40, ridges 62 are provided on the surface of the shape memory alloy hypotube, e.g. as shown in FIG. 8. Ridges 62 provide sharp cutting surfaces for stent 40. Ridges 62 can be formed by EDM machining of the shape memory alloy hypotube prior to laser machining. Alternatively, ridges 62 can be formed by drawing the shape memory alloy hypotube through a die prior to laser cutting. The hypotube is then cut into stent portions, placed over an expanding mandrel, heated and quenched as discussed above.

Typically, after laser machining but before heating and quenching, one cleans the hypotube, e.g. using a bead blaster in conjunction with alumina particles. However, this cleaning process can be performed at other points during the manufacturing process.

Guide wire 36 is typically about 150 cm long, sheath 38 is typically about 135 cm long, shaft 39 is typically about 135 cm long, and the distance between distal end 32a and proximal end 32b of screw 32 is about 170 cm. However, these dimensions are all exemplary, and other sizes and dimensions can be used.

In one embodiment, the proximal end of sheath 38 and shaft 39 are connected to a handle 70 (shown in cross section in FIG. 10) for facilitating motion of sheath 38 relative to shaft 39. Handle 70 comprises a body portion 72 affixed to shaft 39 and a movable control element 74 capable of moving in direction P or D relative to body portion 72. Control element 74 is affixed to sheath 38. Therefore, moving control element 74 relative to handle body portion 72 results in motion of sheath 38 relative to shaft 39 (and therefore motion of sheath 38 relative to stent 40).

Figure 10:
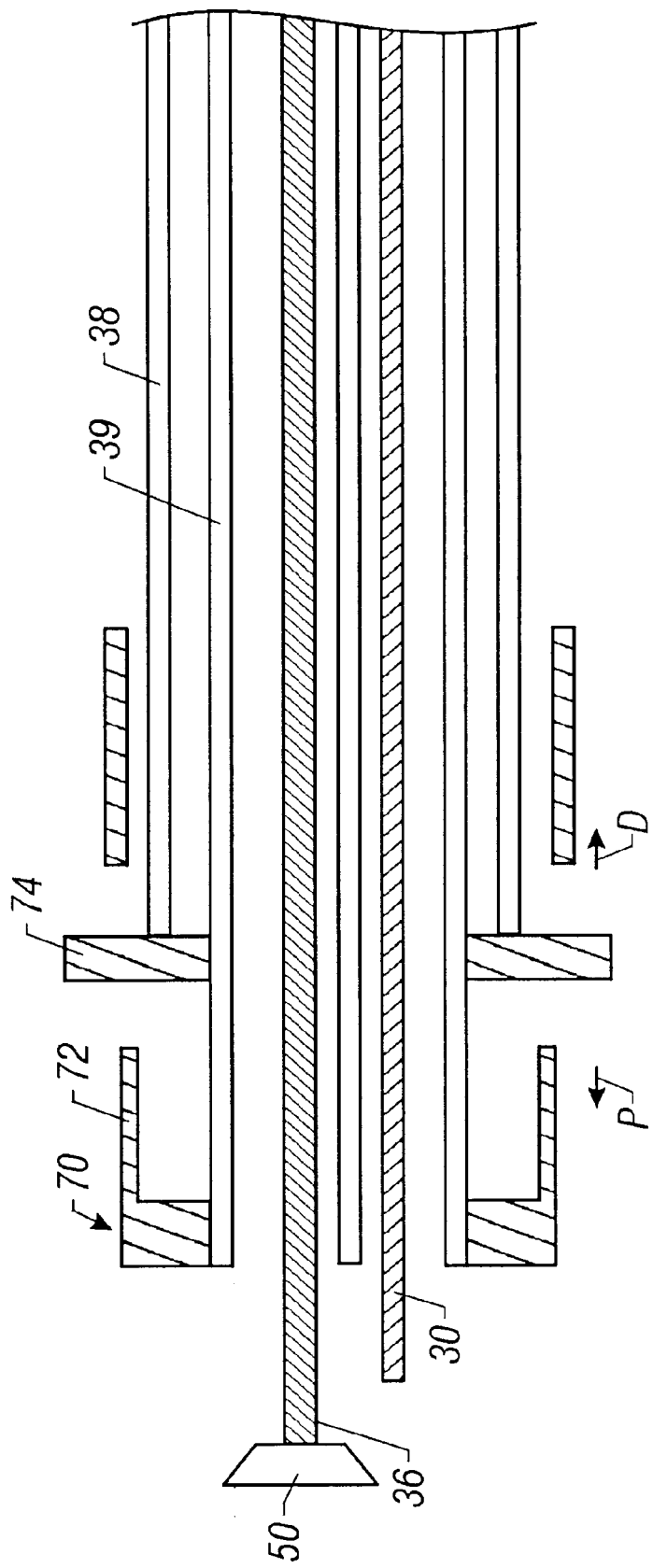
FIG. 10 illustrates in cross section a handle for facilitating control of the position of a catheter sheath relative to a temporary cutting stent.

As seen in FIG. 10, shaft 39 extends through the length of handle 70. The lumens of shaft 39 extend through handle 70, thereby permitting guide wire 30 and screw 36 to exit at the proximal end of handle 70.

Figure 2:
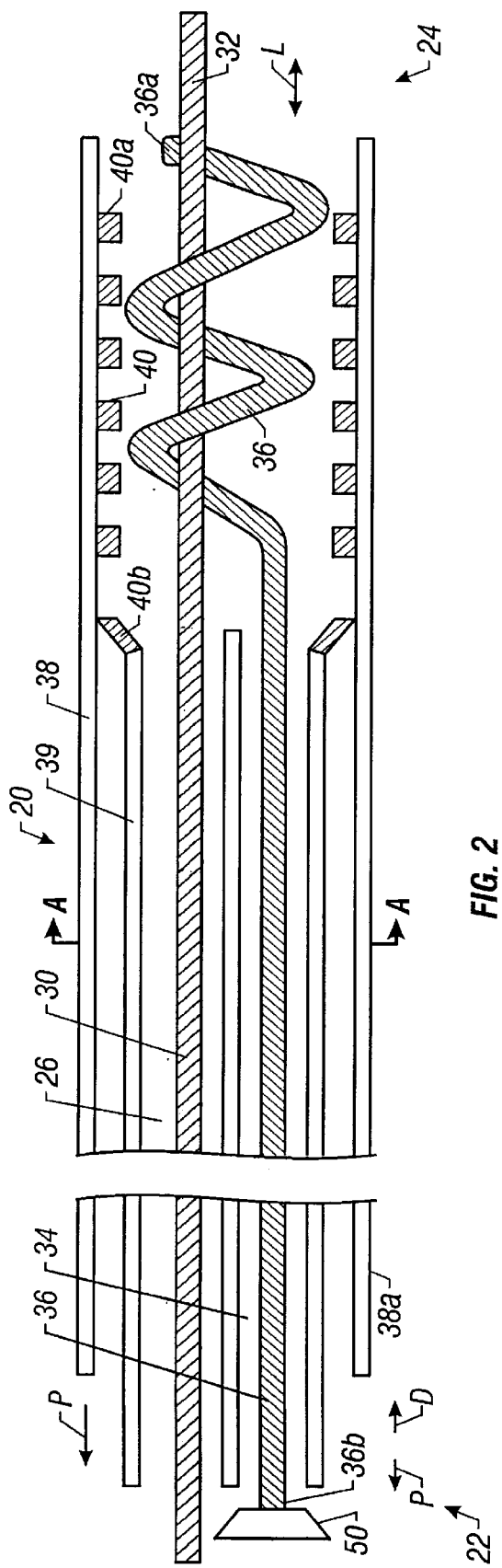
FIG. 2 illustrates in cross section a catheter constructed in accordance with a first embodiment of my invention.
Figure 2A:
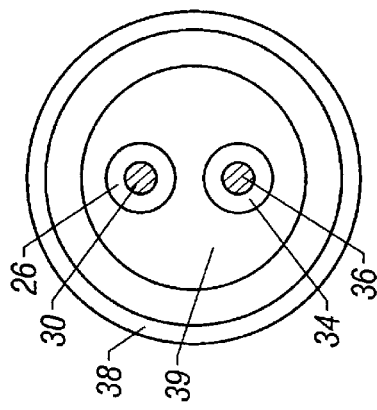
FIG. 2A illustrates in cross section the catheter of FIG. 2 along lines A—A.
Figure 4:
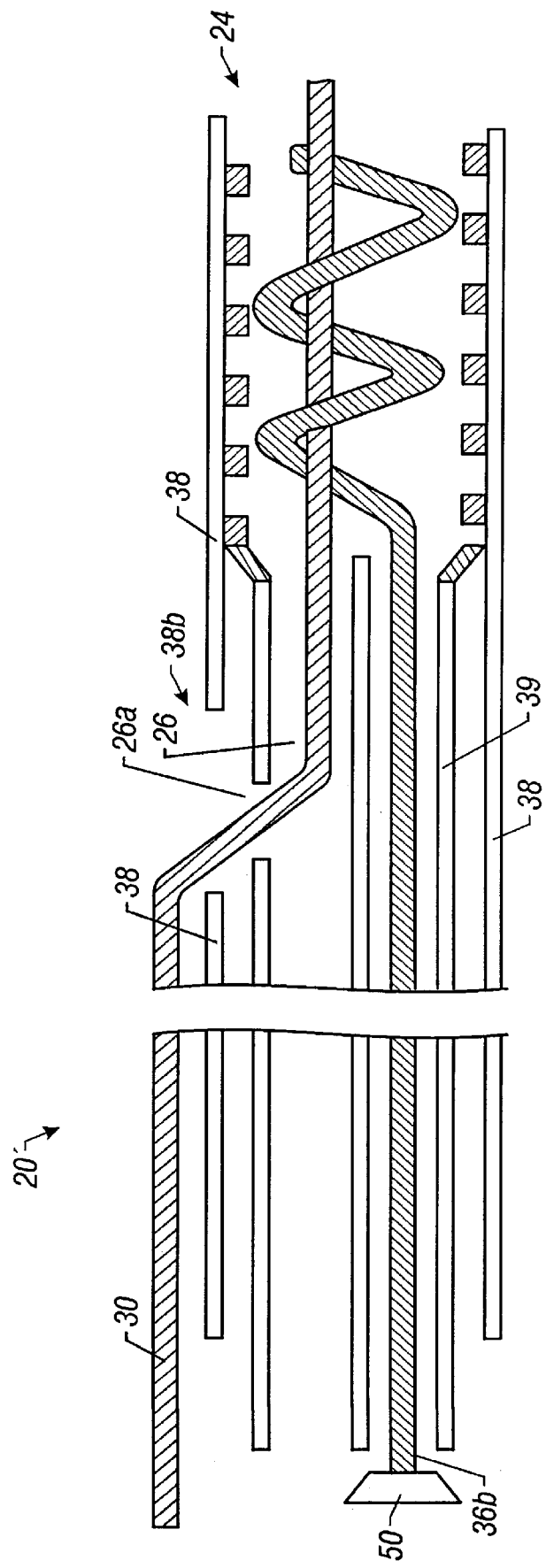
FIG. 4 illustrates a modified embodiment of the catheter of FIGS. 2 and 3 in which the guide wire does not extend through the entire length of the catheter.

FIG. 4 illustrates in cross section a rapid exchange version 20' of the catheter of FIGS. 2 and 3. Referring to FIG. 4, guide wire lumen 26 includes an exit port 26a which permits guide wire 30 to exit lumen 26 relatively close to distal end 24 of catheter 20'. In one embodiment, port 26a is between 10 and 35 cm from distal end 24 of catheter 20'. (Guide wire 30 also exits through a slit 38b in sheath 38 between about 10 and 35 cm from distal end 24 of catheter 20'.)

Of importance, port 26a and slit 38b enable a physician to easily and rapidly exchange catheter 20' with another catheter over guide wire 30. Because guide wire 30 exits between 10 and 35 cm from distal end 24 of catheter 20', catheter 20' can be exchanged over guide wire 30 even though guide wire 30 only extends slightly more than that distance outside the patient. After guide wire 30 and catheter 20' are in place, catheter 20' is withdrawn from the patient and taken off of guide wire 30 while leaving guide wire 30 in place within the patient. Another catheter is then threaded over guide wire 30 and advanced into the patient to a desired location, also without having to remove guide wire 30.

The portion 26b of guide wire lumen 26 proximal to exit port 26a can either remain empty, or can contain a stiffening mandrel or other structure as desired.

Figure 5A:
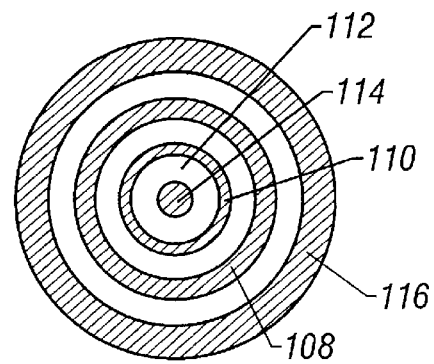
FIG. 5A illustrates in cross section the catheter of FIG. 5 along lines A—A.
Figure 5B:
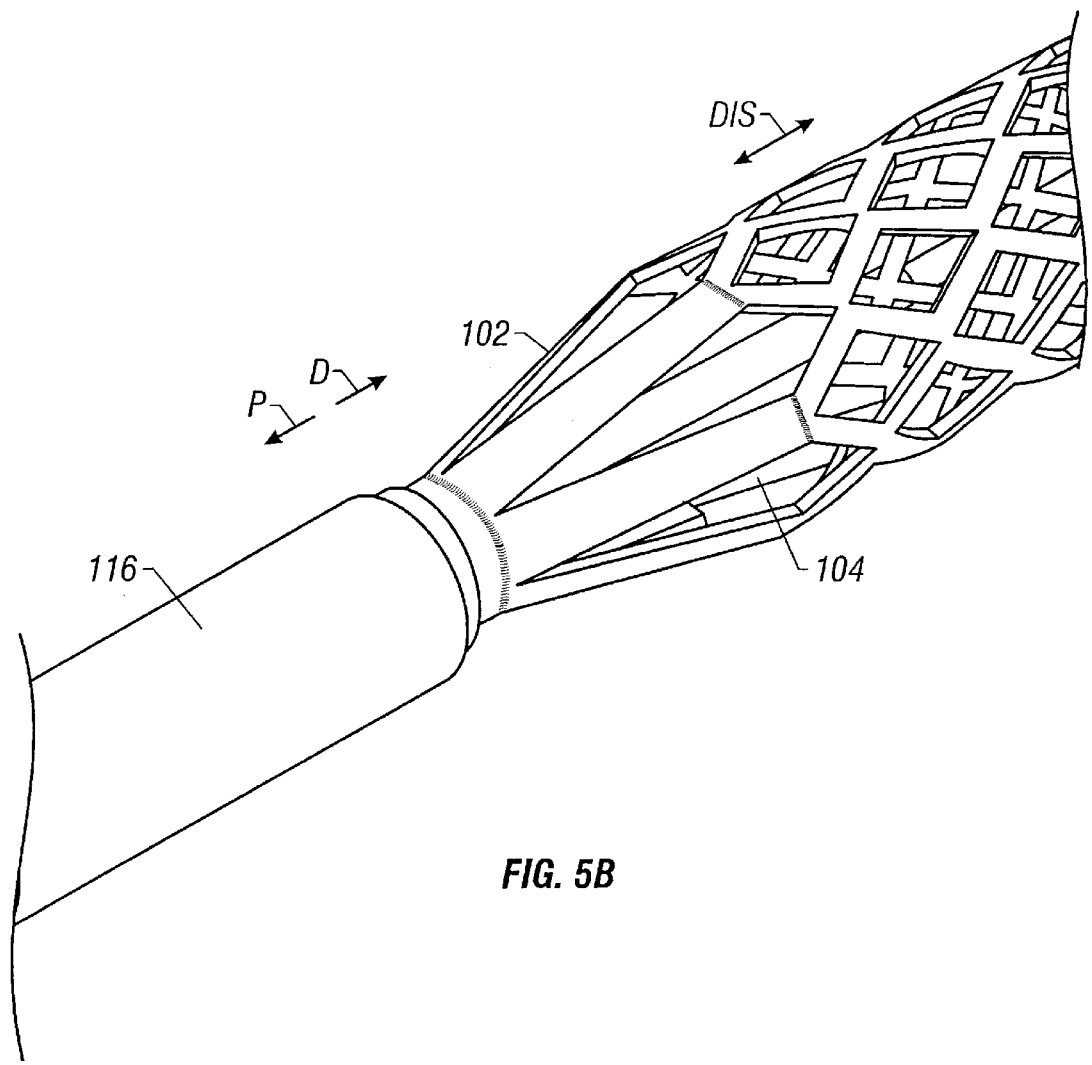
FIG. 5B is an expanded view of a portion of FIG. 5.

FIG. 5 illustrates a second embodiment of my invention including a catheter 100 comprising first and second temporary self-expanding cutting stents 102 and 104 at the distal end of catheter 100. Stents 102 and 104 are made from a shape memory alloy as described above. Stent 104 extends within the interior of stent 102. The proximal end 106 of stent 102 is affixed to a shaft 108 which extends to the proximal end of catheter 100. The proximal end of stent 104 is affixed to a shaft 110 which extends within the lumen of shaft 108. Within shaft 110 is a guide wire lumen 112 through which guide wire 114 is threaded.

Catheter 100 is used as follows. First, a physician threads guide wire 114 through guide wire lumen 112 of catheter 100. Catheter 100 and guide wire 114 are then introduced into and advanced through a patient's vascular system until guide wire 114 is in an appropriate position such that the distal end of guide wire 114 is distal to a constriction within the vascular system. Catheter 100 is then advanced over guide wire 114 until cutting stents 102 and 104 are at a desired location, i.e., within the constriction.

Retractable sheath 116 is then retracted in proximal direction P, thereby exposing stent 102. Stent 102 expands in the same manner as stent 40 described above. Stent 104 also expands to approximately the same diameter as stent 102. Stent 104 is then retracted in proximal direction P to shear off any scar or other tissue extending through the struts of stent 102. The physician accomplishes this by pulling the proximal end of shaft 110 in proximal direction P relative to shaft 108. Of importance, catheter 104 need only be advanced by a distance equal to the distance DIS between the struts of stent 102.

Sheath 116 is then advanced over stents 102 and 104 in distal direction D to collapse stents 102 and 104 and to entrap any cut tissue therein. Catheter 100 is then removed from the artery by retracting catheter 100 in proximal direction P while sheath 116 remains over stents 102 and 104.

Figure 6:
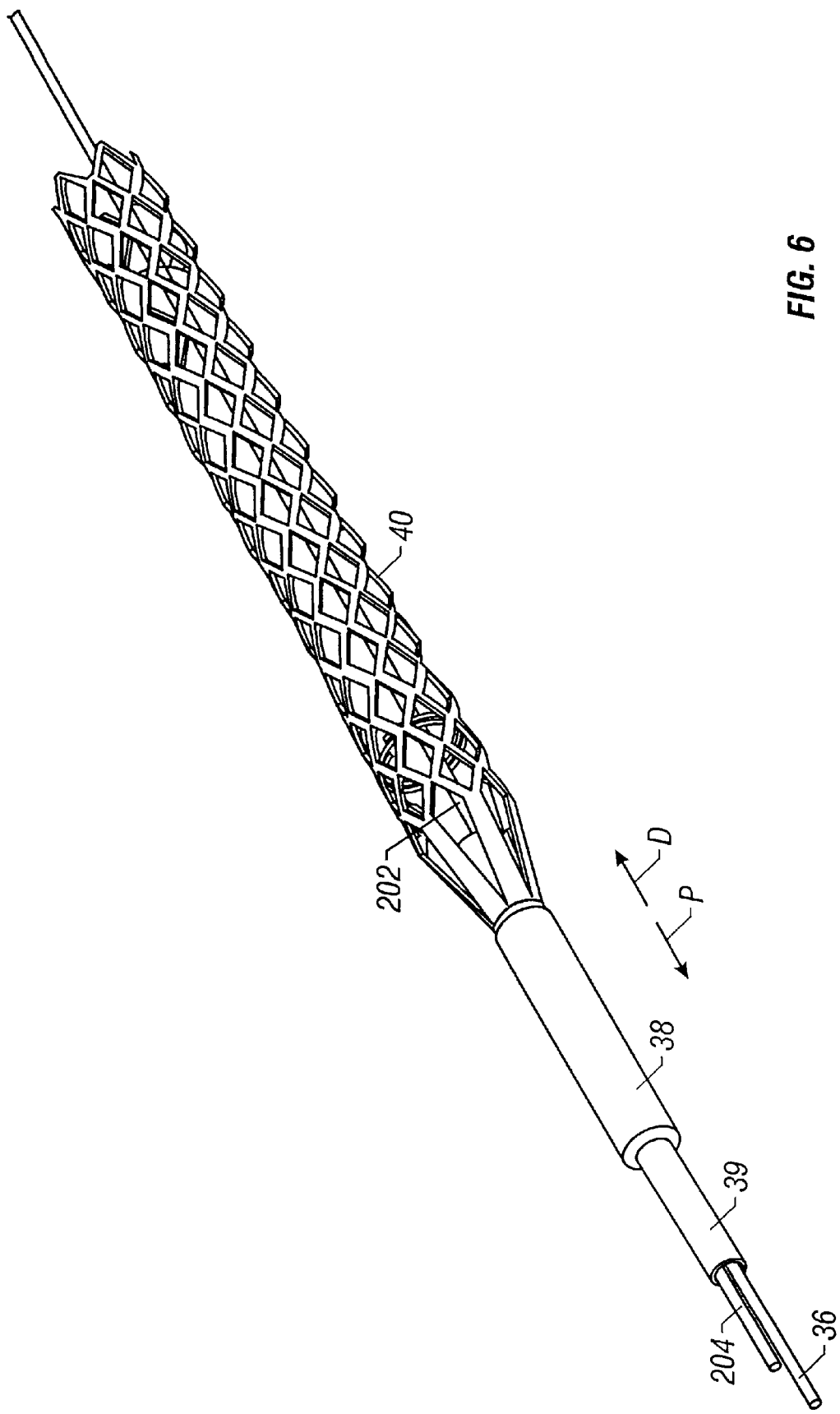
FIG. 6 illustrates the distal end of a catheter constructed in accordance with an embodiment of my invention in which scar tissue extending through stent struts is cut with a ring-shaped cutting tool.
Figure 6A:
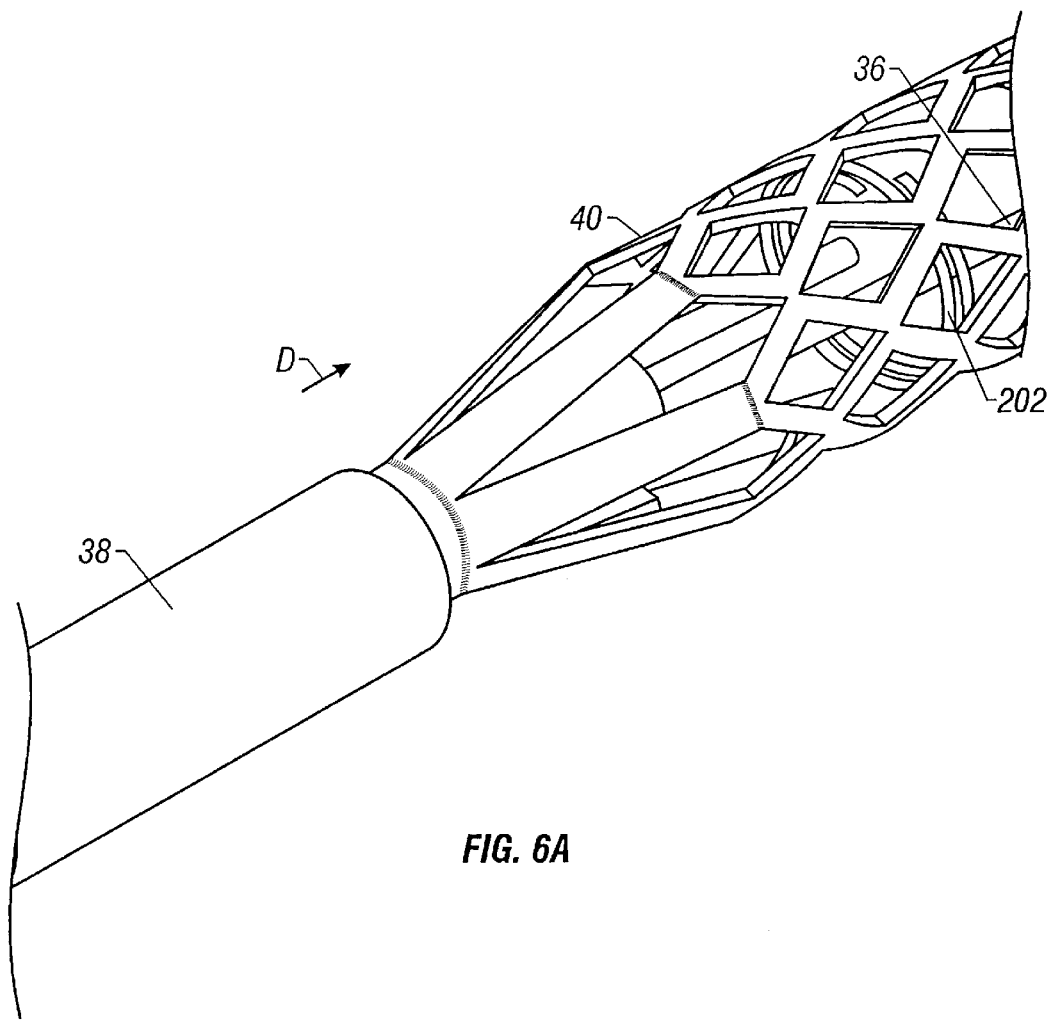
FIG. 6A is an expanded view of a portion of FIG. 6.

FIGS. 6 and 6A illustrate a catheter 200 in accordance with another embodiment of my invention. The catheter of FIG. 6 is similar to that of FIG. 2, except instead of screw 36, a coil 202 extends within temporary cutting stent 40. A thin shaft 204 extends from the proximal end of coil 202. After catheter 200 is in a desired location within the vascular system of the patient, retractable sheath 38 is retracted to expose stent 40 and to permit stent 40 to expand. Stent 40 cuts through any scar or other tissue within the lumen of permanent stent 12 (not shown in FIGS. 6 or 6A, but shown in FIGS. 1A, 1B, 3A and 3B). Thereafter, the attending physician retracts coil 202 in proximal direction P to shear off any scar or other tissue protruding through the struts of stent 40. Coil 202 is retracted by pulling on the proximal end of shaft 204, which extends out of the proximal end of the catheter outside the patient. Sheath 38 is then advanced in distal direction D to collapse stent 40 and coil 202 and encapsulate any tissue therein. Catheter 200 is then withdrawn from the patient.

Figure 7:
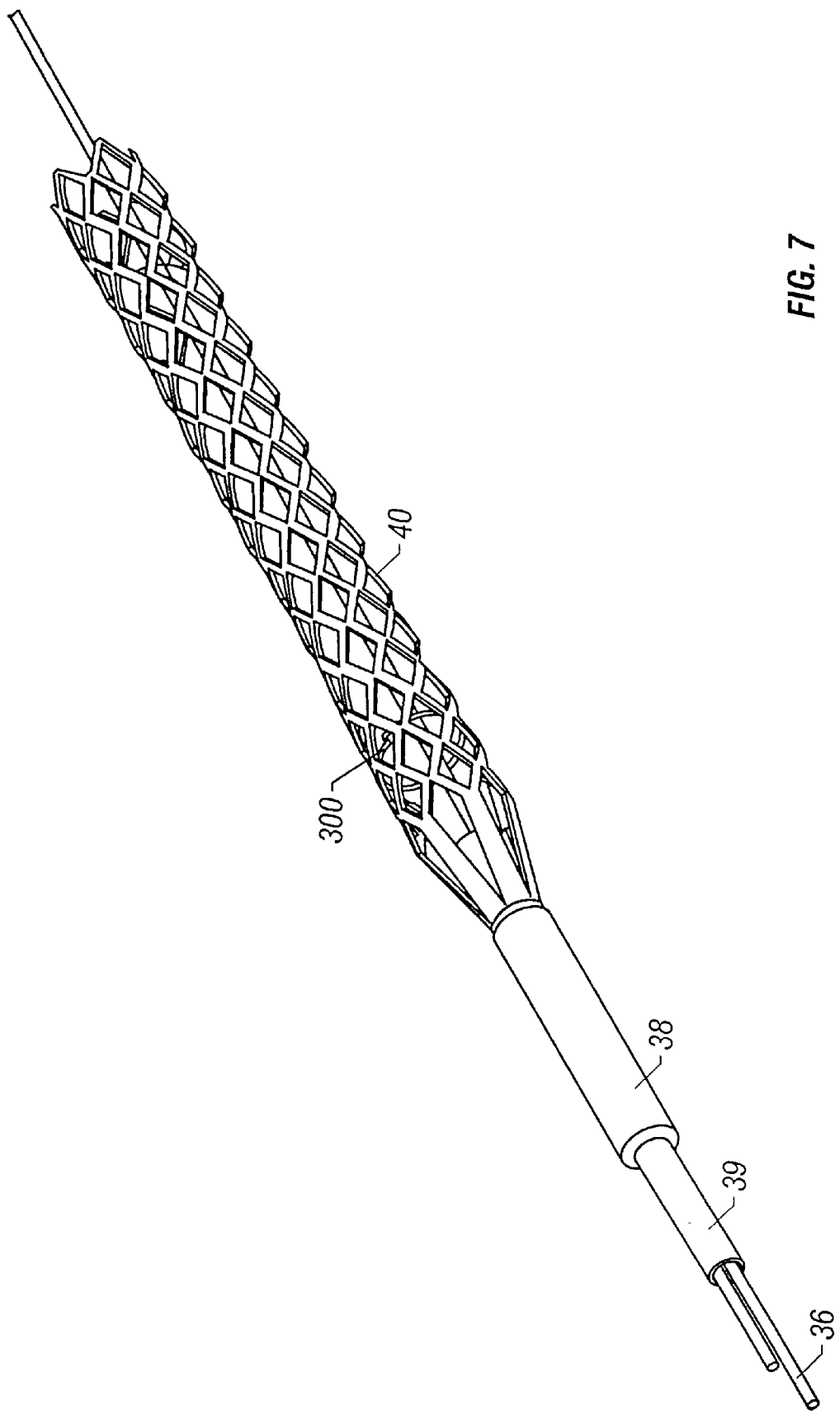
FIG. 7 illustrates the distal end of a catheter constructed in accordance with an embodiment of my invention in which scar tissue extending through stent struts is cut with a coil-shaped cutting tool.
Figure 7A:
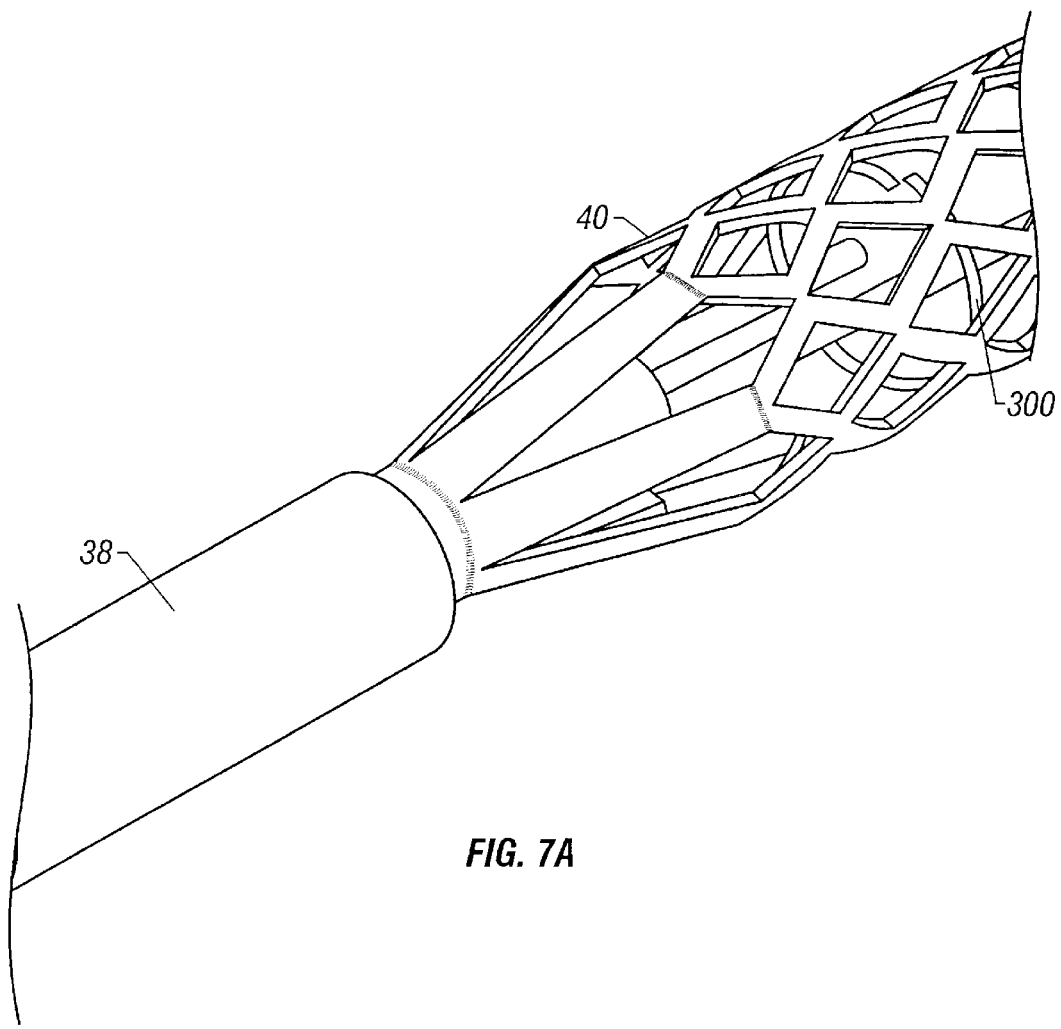
FIG. 7A is an expanded view of a portion of FIG. 7.

FIGS. 7 and 7A illustrate another embodiment of my invention which includes a ring 300 extending from a shaft 302 instead of a coil 202 and shaft 204. The catheter of FIG. 7 is used in the same manner as the catheter of FIG. 6. In either case, coil 202, shaft 204, ring 300 and shaft 302 can be made of a shape memory alloy as discussed above.

These structures can be shaped by appropriate heating and quenching of the shape memory alloy as discussed above.

A catheter in accordance with my invention can be used in either the coronary artery or a peripheral artery. When used in the coronary artery, the attending physician typically first inserts a guiding catheter (not shown) into the patient's vascular system to facilitate positioning of the guide wire and the self-expanding cutting stent catheter. Thereafter, the guide wire and cutting stent catheter are advanced through the guiding catheter and positioned in the patient's coronary artery as described above.

While the invention has been described with respect to specific embodiments, those skilled in the art will recognize that changes can be made in form and detail without departing from the spirit and scope of the invention. For example, the various cutting stents, coils, and screws can be made from shape memory alloys or other appropriate metals or materials. Similarly, shafts 40, 108 and 110 can be made of polyethylene, a stainless steel hypotube, or a shape memory alloy tube to assist in bonding or flexibility. The shafts and sheaths of the catheter can be reinforced with stiffening mandrels or coils to give them desired strength or stiffness. The catheter can be used to remove tissue accumulated within a permanent stent, or tissue that is not within a permanent stent. Accordingly, all such changes come within my invention.

I claim:

1. A catheter comprising:

a self-expanding cutting stent;

a retractable sheath for containing said self-expanding cutting stent, whereby when said retractable sheath is retracted relative to said self-expanding cutting stent, said self-expanding cutting stent expands to cut tissue; and means for pushing against any tissue extending through said self-expanding stent, to thereby cut said tissue.

2. Structure of claim 1 wherein said means for pushing comprises a screw.

3. Structure of claim 1 wherein said means for pushing comprises a second self-expanding stent.

4. Structure of claim 1 wherein said means for pushing comprises a ring.

5. A catheter comprising:

a self-expanding cutting stent;

a retractable sheath for containing said self-expanding cutting stent, whereby when said retractable sheath is retracted relative to said self-expanding cutting stent, said self-expanding cutting stent expands to cut tissue; and a cutting tool which pushes against any tissue extending through said self-expanding cutting stent, to thereby cut said tissue.

6. A method for removing material from a patient's vascular system comprising the steps of:

inserting a catheter into said patient, said catheter comprising an expandable stent at the distal end of said catheter covered by a retractable sheath;

retracting said retractable sheath, thereby exposing said expandable stent and permitting said expandable stent to extend into said material; and withdrawing a member through the interior of said expandable stent to shear off any of said material extending through said expandable stent.

7. Method of claim 6 further comprising the steps of:

pushing said retractable sheath over said expandable stent to collapse said expandable stent; and withdrawing said catheter from said patient.

8. A catheter comprising:

a spring-action stent including a plurality of interconnected struts with open regions between adjacent struts, the struts having cutting edges; and a retractable sheath having a size and shape suitable for containing the springaction stent, the retractable sheath holding the spring-action stent in a coiled configuration when positioned over the spring-action stent, the retractable sheath being retractable from the spring-action stent to release the spring-action coil into an expanded recoil configuration.

9. A catheter according to claim 8 wherein:
the spring-action stent is a tube with an interior lumen and the catheter further includes:
a solid member having an outer surface conformably matched to the spring-action stent interior lumen inner surface, the solid member being moveable within the spring-action stent to shear tissue that extends through the spring-action stent open regions when the spring-action stent is recoiled.

10. A catheter according to claim 9 wherein:
the solid member is a screw.

11. A catheter according to claim 9 wherein:
the solid member is a coil.

12. A catheter according to claim 9 wherein:
the solid member is a ring.

13. A catheter according to claim 8 wherein:
the spring-action stent tube is machined at an angle so that the struts have sharp cutting edges.

14. A catheter according to claim 8 wherein:
the spring-action stent tube is machined at approximately a 90° angle so that the struts have right angle edges.

15. A catheter according to claim 8 further comprising:
a plurality of ridges formed on the spring-action stent tube and machined so that the struts have sharp cutting edges.

16. A catheter according to claim 8 further comprising:
a shaft contained within the sheath; and
a handle formed as a connection between the shaft and the sheath.

17. A method of removing material from walls of a patient's body lumen comprising:
inserting a catheter into the body lumen, the catheter including a spring-action stent and a retractable sheath, the spring-action stent including a plurality of interconnected struts with open regions between adjacent struts, the struts having cutting edges, the retractable sheath having a size and shape suitable for containing the spring-action stent, the retractable sheath holding the spring-action stent in a coiled configuration when positioned over the spring-action stent;
retracting the retractable sheath from the spring-action stent thereby releasing the spring-action coil into an expanded recoil configuration so that the struts press into the material, forcing material into the open regions; and
moving the material relative to the spring-action coil, shearing material in the open regions.

18. A method according to claim 17 wherein moving the material relative to the spring-action coil includes:
moving the catheter relative to the body lumen to shear the material in the open regions.

19. A method according to claim 17 wherein moving the material relative to the spring-action coil includes:
moving a solid member having an outer surface conformably matched to the spring-action stent interior lumen inner surface relative to the spring-action stent to shear tissue that extends through the spring-action stent open regions when the spring-action stent is recoiled.

20. A method according to claim 17 further comprising:
advancing the retractable sheath back over the spring-action stent thereby collapsing the spring-action stent into the coiled configuration and containing the sheared material within the catheter; and
removing the catheter and contained sheared material from the body lumen.

21. A catheter comprising:
a spring-action cutting element including a plurality of interconnected struts with open regions between adjacent struts, the struts having cutting edges; and
a retractable sheath having a size and shape suitable for containing the spring-action cutting element, the retractable sheath holding the spring-action cutting element in a coiled configuration when positioned over the spring-action cutting element, the retractable sheath being retractable from the spring-action cutting element to release the spring-action coil into an expanded recoil configuration.

22. A catheter according to claim 21 wherein:
the spring-action cutting element is a tube with an interior lumen and the catheter further includes:
a solid member having an outer surface conformably matched to the spring-action cutting element interior lumen inner surface, the solid member being moveable within the spring-action cutting element to shear tissue that extends through the spring-action cutting element open regions when the spring-action cutting element is recoiled.

23. A method of removing material from walls of a patient's body lumen comprising:
inserting a catheter into the body lumen, the catheter including a spring-action cutting element and a retractable sheath, the spring-action cutting element including a plurality of interconnected struts with open regions between adjacent struts, the struts having cutting edges, the retractable sheath having a size and shape suitable for containing the spring-action cutting element, the retractable sheath holding the spring-action cutting element in a coiled configuration when positioned over the spring-action cutting element;
retracting the retractable sheath from the spring-action cutting element thereby releasing the spring-action coil into an expanded recoil configuration so that the struts press into the material, forcing material into the open regions; and
moving the material relative to the spring-action coil, shearing material in the open regions.

24. A method according to claim 23 wherein moving the material relative to the spring-action coil includes:
moving the catheter relative to the body lumen to shear the material in the open regions.

25. A method according to claim 23 wherein moving the material relative to the spring-action coil includes:
moving a solid member having an outer surface conformably matched to the spring-action cutting element interior lumen inner surface relative to the spring-action cutting element to shear tissue that extends through the spring-action cutting element open regions when the spring-action cutting element is recoiled.

26. A method according to claim 23 further comprising:
advancing the retractable sheath back over the spring-action cutting element thereby collapsing the spring-action cutting element into the coiled configuration and containing the sheared material within the catheter; and
removing the catheter and contained sheared material from the body lumen.

* * * * *

UNITED STATES PATENT AND TRADEMARK OFFICE
CERTIFICATE OF CORRECTION

PATENT NO. : 6,036,708
DATED : March 14, 2000
INVENTOR(S) : Jason Van Sciver

It is certified that error appears in the above-identified patent and that said Letters Patent is hereby corrected as shown below:

<u>Column 7,</u>
Line 2, change "springaction" to -- spring-action --.

Signed and Sealed this

Seventh Day of May, 2002

Attest:

JAMES E. ROGAN
Attesting Officer        Director of the United States Patent and Trademark Office